| United States Patent [19] | [11] | 4,048,187 |
|---|---|---|
| Anderson et al. | [45] | Sept. 13, 1977 |

[54] 5-(2-HYDROXYPHENYL)TETRAZOLYL COMPOUNDS

[75] Inventors: Brian Anderson; Raymond Frederick Dalton; Philip Martin Rowbotham, all of Manchester, England

[73] Assignee: Imperial Chemical Industries Limited, London, England

[21] Appl. No.: 689,931

[22] Filed: May 25, 1976

[30] Foreign Application Priority Data

June 9, 1975 United Kingdom ............... 24629/75

[51] Int. Cl.$^2$ ..................... C07D 257/04; C07F 1/08; C07F 1/10; C07F 1/12
[52] U.S. Cl. ................................. 260/308 D; 260/299
[58] Field of Search .................................. 260/308 D

[56] References Cited

U.S. PATENT DOCUMENTS

| 3,767,667 | 10/1973 | Kamiya et al. | 260/308 D |
| 3,865,570 | 2/1975 | George et al. | 260/308 D |

Primary Examiner—Frederick E. Waddell
Attorney, Agent, or Firm—Cushman, Darby & Cushman

[57] ABSTRACT 5-(2-Hydroxyphenyl)tetrazoles having substituents containing at least 5 aliphatic or alicyclic carbon atoms are prepared from the corresponding o-hydroxybenzyl cyanides with alkali metal azides. These tetrazoles are useful as extracting agents in liquid-liquid extraction processes for metals, especially copper. When used in such processes in combination with o-hydroxyaryl oximes they improve the extraction kinetics of the oximes.

6 Claims, No Drawings

5-(2-HYDROXYPHENYL)TETRAZOLYL COMPOUNDS

This invention relates to heterocyclic compounds, and more particularly to certain tetrazoles containing hydroxyl groups useful in the extraction of metal values from aqueous solutions of metal salts, especially from such solutions obtained in the course of extracting the metals from their ores.

One of the methods of extracting metals from their ores is to crush the ore and extract it with for example acids to give an aqueous solution of a salt of the desired metal, usually together with salts or other metals also present in the ore. The aqueous solutions may then be treated with an extracting agent, such as a chelating agent, which will react with the salt of the desired metal under the conditions of treatment to form a metal complex compound which is soluble in a water-immiscible organic solvent. The metal is extracted as the complex compound into such a water-immiscible organic solvent. It is convenient to use a solution of the extracting agent in the solvent and to carry out the treatment and extraction simultaneously. It has now been discovered that certain novel tetrazoles containing hydroxyl groups are especially valuable as extracting agents in metal extraction processes.

According to the invention there are provided heterocyclic compounds of the formula

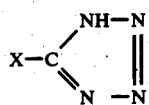

wherein X is an optionally substituted o-hydroxyphenyl group of the formula

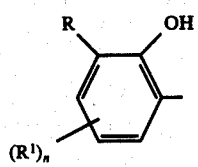

wherein R is a hydrogen or halogen atom or an alkyl group or an electron-withdrawing group and $R^1$ is a hydrogen atom, or an optionally substituted hydrocarbon group attached directly or through an oxygen atom to the benzene ring, n is 1 or 2, with the proviso that the compound contains a total of at least 5 aliphatic or alicyclic carbon atoms.

It will be understood that, although in the formula (I) the hydrogen atom has been placed on the nitrogen atom in position 1 of the ring, the formula could have been expressed with the hydrogen atom placed on a nitrogen atom in position 2 and that compounds to which such an alternative formula are ascribed come within the heterocyclic compounds of the invention.

R is preferably a hydrogen atom. by R there may be mentioned methyl, ethyl, isopropyl, n-butyl, isobutyl, tert.-butyl, amyl, heptyl, octyl, nonyl, undecyl and dodecyl, but preferably a lower alkyl group containing from 1 to 5 carbon atoms.

As examples of halogen atoms which may be represented by R there may be mentioned bromine and particularly chlorine.

As examples of electron-withdrawing groups there may be mentioned nitro. Such groups or halogen atoms tend to increase the stability of the metal complexes and permits the extraction of metals from aqueous solutions at lower pH.

As groups $R^1$ there may be mentioned hydrocarbon groups which are alkyl groups which may be primary, secondary or tertiary and unbranched or, preferably, branched such as methyl, ethyl, isopropyl, n-butyl, isobutyl, tert.-butyl, amyl, heptyl, octyl, nonyl, undecyl and dodecyl, alkenyl groups such as allyl and propenyl, cycloalkyl groups such as cyclohexyl, aryl groups such as phenyl, o-, m- and p-tolyl, substituted hydrocarbon groups such as benzyl, and any of the above groups attached to the benzene ring through an oxygen atom. It is preferred that the group $R^1$ contains at least 5 carbon atoms and provides at least a major part of the necessary aliphatic or alicyclic carbon atoms.

n is preferably 1. In those cases in which n is 2 the two groups $R^1$ may be the same or different.

Of particular value in metal extraction processes owing to their enhanced solubility in water-immiscible solvents are mixtures of heterocyclic compounds whether prepared by mixing separately prepared heterocyclic compounds or, more conveniently, by manufacturing the compounds from a starting material which is a mixture. Especially valuable mixtures of heterocyclic compounds are those in which the components of the mixture have different groups $R^1$, and particularly in which the $R^1$ groups are isomeric. A preferred type of mixture is that derived from p-nonylphenol, wherein the nonyl groups are tertiary nonyl groups, obtained from phenol by alkylation with propylene trimer.

The groups $R^1$ may be in any free position of the benzene ring but preferably in the position para to the hydroxyl group or to the point of attachment of the benzene ring to the tetrazole ring.

As examples of groups X in the heterocyclic compound of the invention there may be mentioned 2-hydroxy-5-nonylphenyl-, 2-hydroxy-3,5 di tert.-amylphenyl-, 2-hydroxy-5-heptylphenyl-, 2-hydroxy-3-chloro-5-nonylphenyl-, 2-hydroxy-4-nonyloxyphenyl-, 2-hydroxy-4-dodecyloxyphenyl-, and 2-hydroxy-4-methyl-5-nonylphenol.

Mixtures of the heterocyclic compounds of the invention are also features of the invention.

The preferred heterocyclic compounds of the invention are those containing from 5 to 18, and especially from 7 to 12, aliphatic or alicyclic carbon atoms.

According to the invention there is also provided a process for the manufacture of heterocyclic compounds of the invention which comprises reacting a nitrile of the formula X-CN, wherein X has the meaning given hereinbefore, with a metal azide in an organic solvent.

As metal azide there may be mentioned especially an alkali metal such as sodium azide which should preferably be used in molar proportions of at least 1 mol. per mol. of nitrile.

An organic solvent there may be mentioned especially solvents in which the metal azide has appreciable solubility, for example dimethylformamide or dimethylsulphoxide.

The process is assisted by the addition of an ammonium salt such as ammonium chloride in equimolar proportion to the metal azide. In this case it is desirable to add a little water to the reaction to prevent sublimation of ammonium azide.

Suitable reaction temperatures are from ambient to 130° C and preferably 120–130° C. Lower reaction temperatures may be used especially with nitriles containing electron-withdrawing groups.

Alternatively the reaction may be carried out in an acidic solvent such as acetic acid at the boiling point. This procedure is more satisfactory in those cases in which the nitrile contains an electron-withdrawing group.

The heterocyclic compound may conveniently be isolated by adding the reaction product to water, extracting the compound with a water-immiscible solvent such as chloroform, and extracting the product from the solvent with aqueous sodium hydroxide. Acidification of the sodium hydroxide extract gives the heterocyclic compound which may be isolated by solvent extraction and removal of the solvent e.g. by heating under reduced pressure.

According to a further feature of the invention there is provided a process for extracting metal values from aqueous solutions which comprises treating the aqueous solution with a heterocyclic compound of the invention and extracting the metal in the form of a complex with the heterocyclic compound from the aqueous solution with a water-immiscible organic solvent.

The process may conveniently be carried out by bringing together the aqueous solution containing the metal values, usually in the form of a salt of the metal or metals and a solution of the heterocyclic compound in the water-immiscible organic solvent at a suitable temperature conveniently ambient temperature, agitating or otherwise disturbing the mixture of liquids so that the area of the water-solvent interfacial layer is increased in order to promote complex formation and extraction, and then decreasing the agitation or disturbance so that the aqueous and solvent layers settle and can be conveniently separated. The process may be carried out in a batchwise manner or preferably continuously, in either case the solvent being if desired stripped of the metal content before re-use, for example by extraction with aqueous acid.

The relative amounts of organic solvent and aqueous solution may be varied widely as desired to be suitable in each case. It is, however, preferred especially when operating the process continuously, to bring together approximately equal volumes of the organic solution and the aqueous solution, adjusting the relative throughputs of the liquid phases, if necessary, by recycling one through the mixing and separating processes.

The amount of heterocyclic compound in relation to the amount of metal may be varied as desired between wide limits, although if a deficiency of heterocyclic compound is used only partial removal of the metal can be achieved in a single extraction step. It is preferred to commence with a molar excess, for example up to 50%, of the heterocyclic compound. The ratio of unextracted metal to free heterocyclic compound will usually alter as the extraction proceeds.

Since formation of the neutral complex compound usually involves the liberation of acid it may be desirable to add e.g. alkali during the process in order to maintain the pH within the desired group.

As organic solvent there may be used any mobile organic solvent or mixture of solvents which is immiscible with water and, under the pH conditions used, inert to water, to the metallic compounds, and to the heterocyclic compound. Especially valuable solvents are aliphatic, alicyclic and aromatic hydrocarbons, which are free flowing, preferably of high flash point, such as kerosine, and mixtures of these, and also chlorinated hydrocarbons such as perchloroethylene, trichloroethane, trichloroethylene and chloroform. Other water immiscible solvents such as esters and ethers may be used but may in some cases cause complications by themselves forming complexes with the metal.

In order to facilitate separation of the aqueous and solvent phases it is desirable to use a solvent having a different density from that of the aqueous layer.

The process may be applied to the extraction of any metal which under the conditions of use, and in particular the pH of the aqueous solution, will form with the heterocyclic compound a stable neutral complex which will dissolve in, or will completely associate with, the organic solvent. The stability of such complexes under various pH conditions will depend primarily on the metal, that from divalent copper being the most stable and complexes from other divalent metals such as nickel, cobalt, zinc and iron being progressively less stable to acid conditions. The formation of stable neutral complexes in the process of the invention is not restricted to metals in the divalent stage or to the above metals and other metals which may form such, complexes include vanadium, tin, cadmium, silver, gold and mercury The process of the invention is particularly suitable for the extraction of copper from aqueous solutions leached from ores containing this metal since the heterocyclic compounds of the invention form stable metal complexes with copper at the low pH values normally associated with these leach liquors. By operating at a pH less than 3, or in the cases wherein R is an electron-withdrawing group or a halogen atom such as bromine at a lower pH, copper may be extracted substantially free from nickel, cobalt and iron.

Owing to the enhanced solubility of the compounds themselves and, especially, their metal complexes in the water-immiscible solvents, mixtures of the heterocyclic compounds of the invention are particularly valuable in the metal extraction process.

The solubility of the compounds and especially their metal complexes may also be increased by the addition of an alkyl phenol, especially an alkyl phenol having an alkyl group containing from 4 to 12 carbon atoms such as p-nonylphenol. Phenol itself and lower alkyl phenols are not satisfactory in a continuous process since their solubility in water is such that they would be removed from the continuous system in the aqueous phase.

If desired other compounds, such as long chain ($C_8$–$C_{12}$) aliphatic alcohols, which may modify the formation and extraction of the complex compound or assist in the subsequent isolation of the metal from the organic solvent, or in the separation of the organic and aqueous phase may also be present.

The addition of surface active agents such as ethylene oxide/alkyl phenol condensate is sometimes desirable in order to assist separation of the aqueous and organic phases by reducing any tendency to emulsification.

The metal may be isolated from the solvent after the extraction stage by any conventional process, for example by extraction into an aqueous phase under pH conditions, for example acidic conditions, in which the complex is unstable. Such a treatment will regenerate the heterocyclic compound and the solvent containing heterocyclic compound so recovered may conveniently be re-used in the process, especially when operated continuously. The heterocyclic compounds in which R is a halogen atom or electron-withdrawing group will usually require stronger acid for regeneration than those in which R is a hydrogen atom. The latter for example when used for extraction of copper values may be extracted satisfactorily with an aqueous solution containing 150 g. per liter of sulphuric acid but more strongly acid solutions may be required for the former class of heterocyclic compounds.

The heterocyclic compounds of the invention are particularly valuable in metal extraction proecesses owing to their high stability to hydrolysis under the acidic conditions usually prevailing in such processes and especially because of the exceptionally high rate of transferring metals from the aqueous to organic phase. This latter property is found also in mixtures of the heterocyclic compounds with other extracting agents such as substituted, particularly alkyl substituted, o-hydroxyphenyl ketoximes, for examples those of British Pat. Nos. 1091354 and 1322532, U.S. Pat. No. 3655347, Belgian Pat. Nos. 804030 and 804031, and German Offenlegungsschrift 2407200, and o-hydroxyphenylaldoximes of Belgian Pat. No. 796835. These oximes are used in metal extraction processes in a manner similar to the heterocyclic compound of the invention. Even a small amount of a heterocyclic compound, for example as little as 3% in one of these oximes will bring about a significant improvement in the kinetics of extraction of the oxime. Preferred amounts are up to 30%, especially from 1 to 15%, of heterocyclic compound based on oxime, which itself is used in from 2 to 50% solution. Such synergistic mixtures of the heterocyclic compounds and other metal extracting agents and the use of such mixtures in metal extraction processes represent further features of the invention.

The process of the invention may be applied especially to aqueous solutions resulting from treatment of mineral ores, scrap metal or other metal-containing residues with aqueous acids such as sulphuric, sulphurous, hydrochloric, or nitric acids or for example with aqueous ammonia or ammonium carbonate or to metal containing spent liquors from electrolytic or chemical processes.

This invention is illustrated but not limited by the following Examples in which all parts and percentages are by weight unless otherwise stated.

EXAMPLE 1

A mixture of 13.5 parts of 2-hydroxy-5-nonyl benzonitrile, 3.6 parts of sodium azide and 2.95 parts of ammonium chloride, 50 parts of dimethyl formamide and 0.5 parts of water was stirred and boiled for four hours. After cooling the mixture was diluted with water and extracted into chloroform. The chloroform solution was washed with water and with 2 × 200 mls of a 2N solution of sodium hydroxide to extract the product. The aqueous alkaline solution was neutralised with 2N sulphuric acid and re-extracted with chloroform. The extract was washed with water, dried, and evaporated to give 7.1 parts of 5-(2-hydroxy-5-nonylphenyl)tetrazole.

On analysis the product was found to contain 65.3% of carbon; 8.1% of hydrogen and 19.4% of nitrogen. Required for $C_{16}H_{24}N_4O$; 66.7% of carbon, 8.3% of hydrogen and 19.4% of nitrogen.

The 2-hydroxy-5-nonylbenzonitrile used in the above example was prepared as follows:

A solution of 52.6 parts of 2-hydroxy-5-nonyl-benzaldoxime (in which the nonyl group is a mixture of branched chain isomers; prepared as described in Example 1 of Belgian Pat. No. 796835) in 60 parts of acetic anhydride was stirred and boiled for 1 hour. The cooled solution was poured into water, stirred for 30 minutes and extracted into 2 × 150 parts of chloroform. The extracts were washed with water, dried over anhydrous magnesium sulphate and evaporated at 50° C under vacuum to yield 61.6 parts of 2-acetoxy-5-nonylbenzonitrile as a brown oil. The 61.6 parts of the acetoxy compound were mixed with 200 parts of ethanol and 300 parts of a 2N solution of sodium hydroxide and the mixture stirred and boiled under reflux for 1½ hours. The cooled solution was acidified with hydrochloric acid, diluted with water and extracted into chloroform. The extracts were water washed, dried over anhydrous magnesium sulphate and evaporated to give 53.1 parts of 2-hydroxy-5-nonylbenzonitrile as a brown oil.

EXAMPLE 2

50 Parts by volume of a chloroform solution containing 2.27 parts by weight of the product of Example 1 were shaken for 15 minutes with 100 parts by volume of an aqueous solution containing 3.0 g. per liter of copper as the sulphate at pH 2.0. Analysis of the loaded extractant solution showed it to contain 3.84 g. of copper per liter.

40 Parts of the copper loaded extractant solution were contacted with two successive 40 part by volume portions of a solution containing 200 g. of sulphuric acid and 30 g. of copper per liter. Analysis of the stripped organic phase showed that it contained no detectable amount of copper.

EXAMPLE 3

50 Parts by volume of a chloroform solution containing 7.05 parts by weight of the product of Example 1 were contacted for 30 seconds under controlled stirring conditions with 50 parts of an aqueous solution containing 7 g. per liter of copper at pH 2.0. The phases were allowed to separate and a portion of each removed for analysis. Stirring was then recommenced and maintained for a total of 15 minutes to establish equilibrium. Again portions of each phase were analysed for copper, and the approach to equilibrium in 30 seconds calculated. Similar experiments were carried out with commercially available hydroxy oxime type extractants in perchloroethylene and the results are as shown below.

| Extractant | Approach to Equilibrium in 30 Seconds |
| --- | --- |
| Product of Example 1 | 95.4% |
| Alkyl-2-hydroxybenzophenoneoxime commercially available as a metal extractant | 57.0 |
| Alkyl-2-hydroxyphenylbenzylketoxime, Example 1 of Belgian Patent No. 804,030 | 57.9 |

EXAMPLE 4

75 Parts by volume of a kerosine solution containing 140 g. liter of the hydroxyoxime type copper extractant of Example 1 of Belgian Pat. No. 804,030 and 10 g. per liter of the heterocyclic compound of Example 1 were contacted under controlled stirring conditions with 50 parts by volume of an aqueous solution containing 10 g. of copper, 10 g. of sulphuric acid, and 200 g. of magnesium sulphate heptahydrate per liter. This procedure was repeated with fresh solutions for various time intervals, each time the phases being separated and analysed for copper content to give the approach to equilibrium as a function of time.

For comparison the above experiment was repeated but without the addition of the heterocyclic compound of Example 1 to the organic phase. The results shown in the table below clearly demonstrate the much faster extraction obtained by the addition of a small quantity of the heterocyclic compound.

| Time | % Approach to Equilibrium | |
|---|---|---|
| | With heterocyclic compound | With heterocyclic compound |
| 10 sec. | 83.4 | 56.3 |
| 20 sec. | 92.3 | 68.7 |
| 30 sec. | 96.9 | 79.9 |
| 60 sec. | 98.3 | 91.6 |
| 120 sec. | 99.7 | 96.3 |
| 15 min. | 100 | 100 |

EXAMPLE 5

400 Parts by volume of a kerosene solution containing 50 g. per liter of the hydroxyoxime type copper extractant of Example 1 of Belgian Patent No. 804030 and 3 g. per liter of the heterocyclic compound of Example 1 were contacted with 400 parts of an aqueous solution containing 3 g. per liter of copper as copper sulphate at pH 2.0 under controlled stirring conditions. The dispersion was sampled at suitable time intervals and each phase analysed for copper.

The experiment was repeated without the addition of the heterocyclic compound and the results expressed as approach to equilibrium as a function of time are shown below.

| Time | % Approach to Equilibrium | |
|---|---|---|
| | With heterocyclic compound | Without heterocyclic compound |
| 15 sec. | 92.8 | 58.2 |
| 30 sec. | 98.4 | 74.6 |
| 45 sec. | 99.2 | 84.5 |
| 60 sec. | 99.7 | 91.1 |
| 90 sec. | 99.3 | 95.2 |
| 120 sec. | 99.6 | 98.2 |
| 15 min. | 100 | 100 |

EXAMPLE 6

The procedure of Example 1 is repeated using 12.0 parts of 2-hydroxy-5-heptyl benzonitrile instead of the 5-nonyl compound to give 6.3 parts of 5-(2-hydroxy-5-heptylphenyl)tetrazole.

On analysis, the product was found to contain 64.7% of carbon, 8.1% of hydrogen and 19.8% of nitrogen. Required for $C_{14}H_{20}N_4O$: 64.6% of carbon, 7.7% of hydrogen and 21.5% of nitrogen.

EXAMPLE 7

The procedure of Example 1 is repeated using 14.2 parts of 2-hydroxy-3,5-di-tert.-amyl benzonitrile instead of the 5-nonyl compound to give 9.4 parts of 5-(2-hydroxy-3,5-tert-amylphenyl) tetrazole, melting at 184° C.

On analysis the product was found to contain 67.9% of carbon, 9.1% of hydrogen and 18.6% of nitrogen. Required for $C_{17}H_{26}N_4O$: 67.5% of carbon, 8.6% of hydrogen and 18.5% of nitrogen.

The proton ratios (NMR) were as follows:

| | Calculated | Found |
|---|---|---|
| Aromatics | 2.0 | 1.9 |
| Alkyls | 22.0 | 22.1 |

EXAMPLE 8

The procedure of Example 1 is repeated using 17.2 parts of 2-hydroxy-3-bromo-5-nonyl benzonitrile instead of 2-hydroxy-5-nonyl benzonitrile to give 5-(2-hydroxy-3-bromo-5-nonylphenyl)-tetrazole as a golden oil.

The proton ratios (NMR) were as follows:

| | Calculated | Found |
|---|---|---|
| Aromatics | 2.0 | 2.0 |
| Alkyls | 19.0 | 19.1 |

EXAMPLE 9

The procedure of Example 1 is repeated using 2-hydroxy-3-methyl-5-nonyl benzonitrile instead of 2-hydroxy-5-nonyl benzonitrile to give 5-(2-hydroxy-3-methyl-5-nonylphenyl)tetrazole as a brown oil.

EXAMPLE 10

Portions of a solution containing 41 g of the product of Example 1 per liter of solution in Aromasol H, a high flash point aromatic solvent, were contacted by vigorous stirring for 15 minutes at various volume ratios with portions of an aqueous feed solution containing 3.0 g/l of copper as sulphate at pH 2.0. The phases were then separated and analysed for copper content to determine the amount of copper in the organic phase of equilibrium with the aqueous phase. The results were as follows:

| Organic/Aqueous phase ratio | 0.43 | 0.67 | 1.0 | 1.50 | 2.33 | 4.0 |
|---|---|---|---|---|---|---|
| Copper in Organic phase (g/l) | 4.28 | 3.31 | 2.44 | 1.77 | 1.20 | 0.72 |
| Copper in Aqueous phase (g/l) | 1.17 | 0.80 | 0.56 | 0.34 | 0.20 | 0.12 |

These results demonstrate the high distribution of copper into the organic phase.

EXAMPLE 11

400 parts by volume of a solution containing 50 g per liter of 2-hydroxy-4-nonylsalicylaldoxime (the product of Example 1 of Belgian Patent No. 796835) in Aromasol H and 1.0 g per liter of the heterocyclic compound of Example 1 were contacted with 400 parts by volume of an aqueous solution containing 3.0 g per liter of copper as sulphate at pH 2.0 under controlled stirring conditions. The dispersion was sampled at suitable time intervals and each phase separated and analysed for copper.

The experiment was repeated without the addition of the heterocyclic compound and the results for both experiments expressed as a percentage of the approach to equilibrium (assumed to be reached in 15 minutes) as a function of time are shown below.

| Time | % Approach to Equilibrium | |
|---|---|---|
| | With heterocyclic compound | With heterocyclic compound |
| 10 sec. | 86.1 | 53.4 |
| 20 sec. | 93.8 | 67.9 |
| 30 sec. | 92.2 | 76.9 |
| 45 sec. | 98.7 | 82.9 |
| 15 min. | 100 | 100 |

EXAMPLE 12

Solutions were prepared in Escaid 100 (an 80% aliphatic kerosene type solvent) containing 0.1 g.mol. of a ketoxime as listed below and 0.005 g.mol. of the product of Examples 1 or 7 respectively. 25 ml. of each solution were added to 50 ml. of a 0.05 molar aqueous copper sulphate solution at pH 2 stirred at 870 r.p.m. and the dispersion sampled and analysed at intervals of time to determine the time required to attain 50% equilibration. Control experiments in which the product of Example 1 to 7 was omitted were also carried out. Table 1 gives the ratios of the times required without it. The smaller is the figure the more effective is the product in increasing the rate of equilibration. A figure above 1.0 would indicate that equilibration had been hindered.

The ketoximes used were as follows:
A. 5-Nonyl-2-hydroxybenzophenone oxime
B. Benzyl 5-nonyl-2-hydroxyphenyl ketoxime
C. Commercially available 5-nonyl-2-hydroxybenzophenone oxime containing added aliphatic α-hydroxyoxime
D. 3-Chloro-5-nonyl-2-hydroxybenzophenone oxime
E. Methyl-5-nonyl-2-hydroxyphenyl ketoxime.

Table 1

| Heterocyclic Compound | Oxime | | | | |
|---|---|---|---|---|---|
| | A | B | C | D | E |
| Example 1 | 0.37 | 0.36 | 0.5 | 0.55 | 0.37 |
| Example 7 | 0.51 | 0.54 | 0.52 | 0.40 | 0.32 |

We claim:
1. A heterocyclic compound of the formula

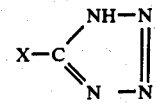

wherein X is a substituted o-hydroxyphenyl group of the formula

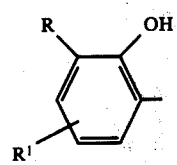

wherein R is hydrogen, halogen, nitro or alkyl and $R^1$ is hydrogen or alkyl, with the proviso that R and $R^1$ together contain from 5 to 18 aliphatic carbon atoms.

2. The heterocyclic compound of claim 1 wherein R is hydrogen.

3. The heterocyclic compound of claim 1 wherein $R^1$ is in the position para to the hydroxyl group.

4. The heterocyclic compound of claim 1 wherein $R^1$ is branched alkyl.

5. A mixture of two or more heterocyclic compounds of claim 1.

6. A mixture of two or more heterocyclic compounds of claim 1 wherein each $R^1$ is a tertiary nonyl group.

* * * * *